United States Patent
Lee

(10) Patent No.: US 10,449,381 B2
(45) Date of Patent: Oct. 22, 2019

(54) LIGHT-MAGNETISM PROVIDING APPARATUS

(71) Applicant: Chung-Ming Lee, Taichung (TW)

(72) Inventor: Wen-Pin Lee, Taichung (TW)

(73) Assignee: Chung-Ming Lee, Taichung (TW)

( * ) Notice: Subject to any disclaimer, the term of this patent is extended or adjusted under 35 U.S.C. 154(b) by 227 days.

(21) Appl. No.: 15/656,535

(22) Filed: Jul. 21, 2017

(65) Prior Publication Data

US 2019/0022402 A1 Jan. 24, 2019

(51) Int. Cl.
*A61N 2/00* (2006.01)
*A61N 5/06* (2006.01)

(52) U.S. Cl.
CPC ............. *A61N 2/002* (2013.01); *A61N 5/06* (2013.01); *A61N 2005/063* (2013.01); *A61N 2005/0632* (2013.01); *A61N 2005/0633* (2013.01); *A61N 2005/0652* (2013.01); *A61N 2005/0654* (2013.01); *A61N 2005/0659* (2013.01)

(58) Field of Classification Search
CPC .... A61N 2/002; A61N 5/06; A61N 2005/063; A61N 2005/0633; A61N 2005/0654; A61N 2005/0652; A61N 2005/0659; A61N 2005/0632
USPC ........................................... 600/9–15, 26–27
See application file for complete search history.

(56) References Cited

U.S. PATENT DOCUMENTS

| | | | | |
|---|---|---|---|---|
| 4,428,366 A | * | 1/1984 | Findl | A61N 2/02 600/14 |
| 5,929,732 A | * | 7/1999 | Bushman | H01F 7/0278 315/5.35 |
| 5,997,464 A | * | 12/1999 | Blackwell | A61N 2/02 600/13 |
| 6,450,941 B1 | * | 9/2002 | Larsen | A61N 1/40 600/14 |
| 7,520,849 B1 | * | 4/2009 | Simon | A61N 2/02 600/14 |
| 2002/0077523 A1 | * | 6/2002 | Ardizzone | A61N 2/06 600/9 |
| 2003/0093915 A1 | * | 5/2003 | Pearl | A61N 5/0617 34/96 |
| 2003/0158585 A1 | * | 8/2003 | Burnett | A61N 1/36021 607/2 |
| 2004/0051503 A1 | * | 3/2004 | Fan | H04M 1/21 320/117 |
| 2005/0075703 A1 | * | 4/2005 | Larsen | A61N 1/40 607/88 |
| 2006/0247742 A1 | * | 11/2006 | Lee | A61H 7/003 607/89 |
| 2008/0288035 A1 | * | 11/2008 | Gill | A61F 7/007 607/108 |

(Continued)

*Primary Examiner* — Navin Natnithithadha
*Assistant Examiner* — Sunita Reddy
(74) *Attorney, Agent, or Firm* — Muncy, Geissler, Olds & Lowe, P.C.

(57) ABSTRACT

A light-magnetism harmonizer is provided, including: a shell body, defining a space and including a magnetism-shielding layer outside the space; a light generator, attached to the shell body, emitting light into the space; a magnetic unit, attached to the shell body and located by an inner side of the magnetism-shielding layer, part of magnetic line of force of the magnetic unit going outwardly being shielded by the magnetism-shielding layer, part of magnetic line of lines of the magnetic unit going inwardly into the space.

9 Claims, 8 Drawing Sheets

(56) References Cited

U.S. PATENT DOCUMENTS

| | | | |
|---|---|---|---|
| 2012/0155087 A1* | 6/2012 | Kim | F21K 9/65 362/249.03 |
| 2016/0074670 A1* | 3/2016 | Mohamed | A61N 2/002 600/14 |
| 2016/0228721 A1* | 8/2016 | Mohamed | A61N 2/002 |

* cited by examiner

LIGHT-MAGNETISM PROVIDING APPARATUS

BACKGROUND OF THE INVENTION

Field of the Invention

The present invention relates to a light-magnetism providing apparatus.

Description of the Prior Art

Recently, people are busy working and lack exercises, and the air is not clean, so it results in worse blood circulation and diseases to nervous system and respiratory passage.

There are magnetic relaxation devices and infrared relaxation devices in the market. However, they each can provide only magnetic or infrared effect, and cannot provide interactive harmonic effect of the magnetism and light, thus having limited effect for blood circulation, mental status and resistance against diseases.

The present invention has arisen to mitigate and/or obviate the afore-described disadvantages.

SUMMARY OF THE INVENTION

The major objective of the present invention is to provide a light-magnetism providing apparatus which can provide light and magnetism.

To achieve the above and other objectives, a light-magnetism providing apparatus is provided, including: a shell body, defining a space and including a magnetism-shielding layer outside the space; a light generator, attached to the shell body, emitting light into the space; a magnetic unit, attached to the shell body and located by an inner side of the magnetism-shielding layer, part of magnetic lines of force of the magnetic unit going outwardly being shielded by the magnetism-shielding layer, part of magnetic lines of force of the magnetic unit going inwardly into the space.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

Figure 1:
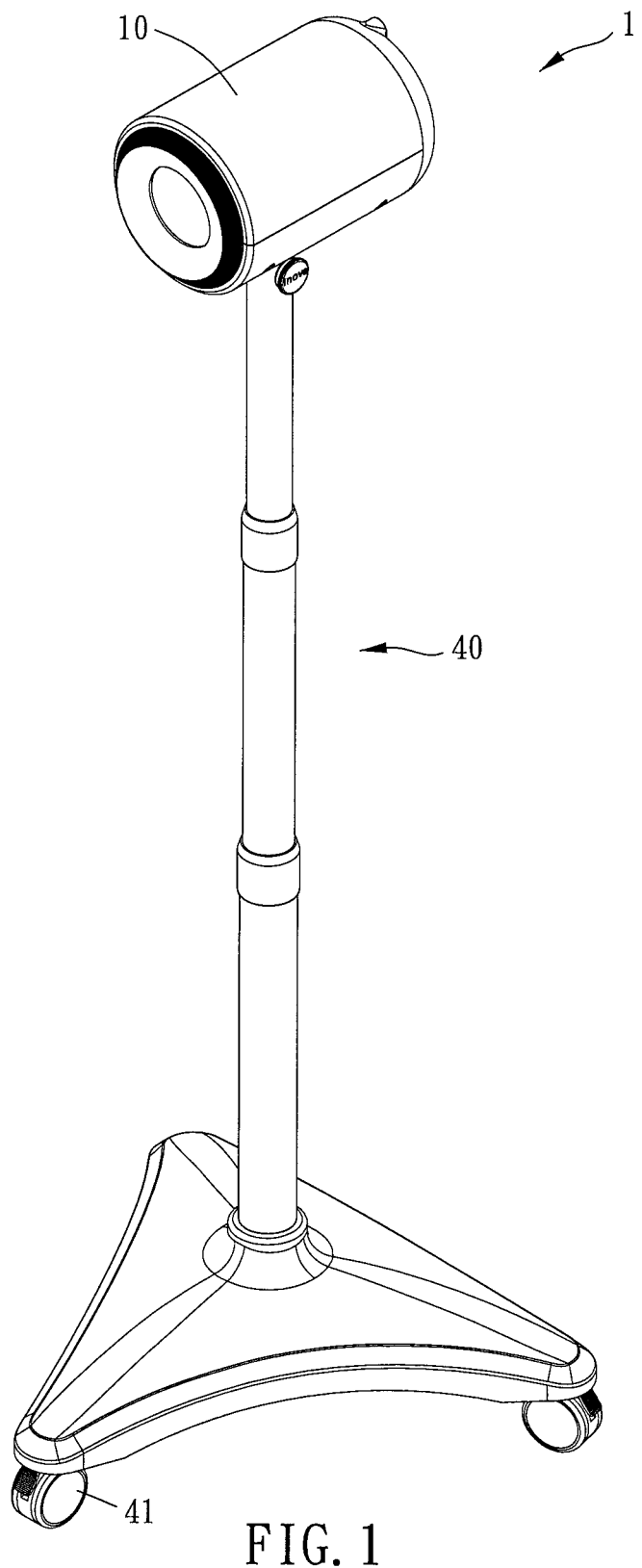
FIG. 1 is a perspective view of a first preferred embodiment of the present invention.
Figure 2:
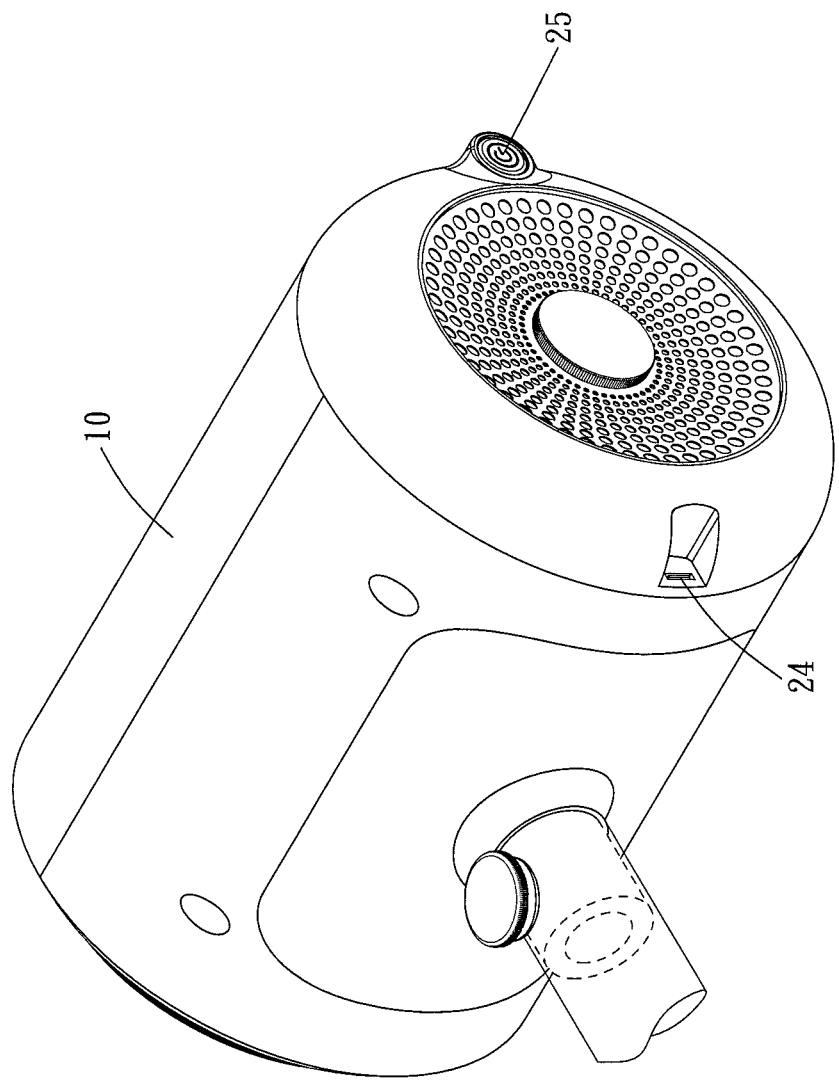
FIG. 2 is a partially-enlarged view of FIG. 1.
Figure 3:
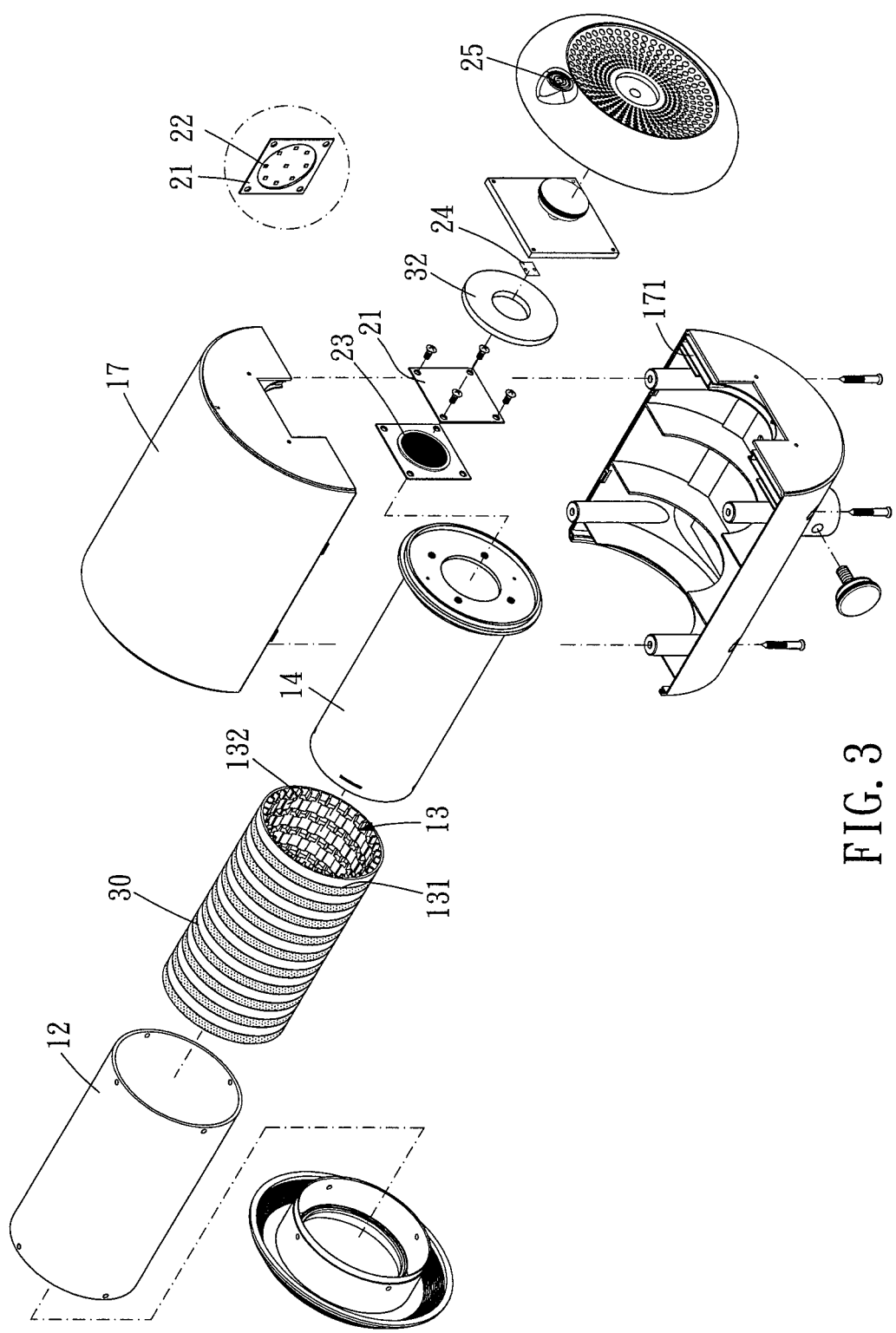
FIG. 3 is a breakdown view of the first preferred embodiment of the present invention.
Figure 5:
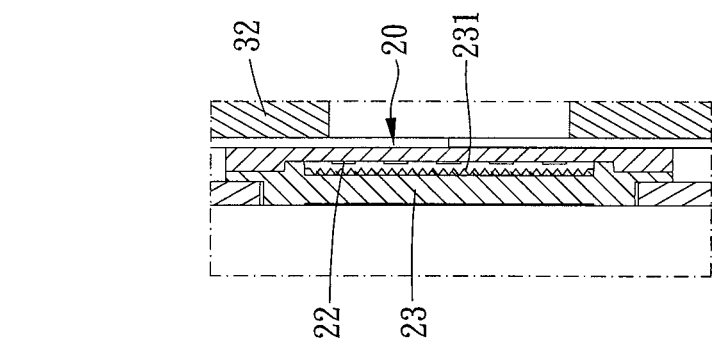
FIG. 5 is a partially-enlarged view of FIG. 4.
Figure 4:
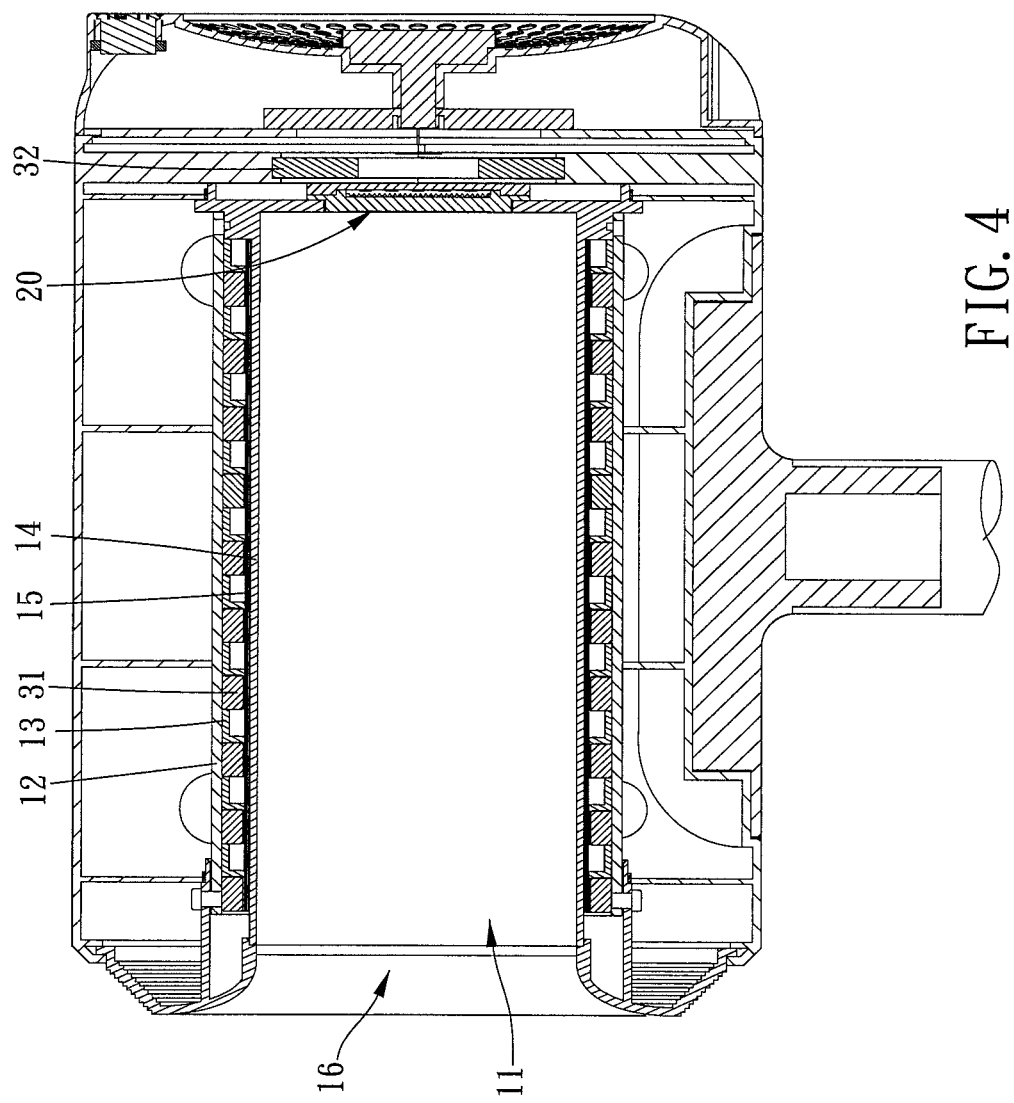
FIG. 4 is a cross-sectional view of the first preferred embodiment of the present invention.
Figure 6:
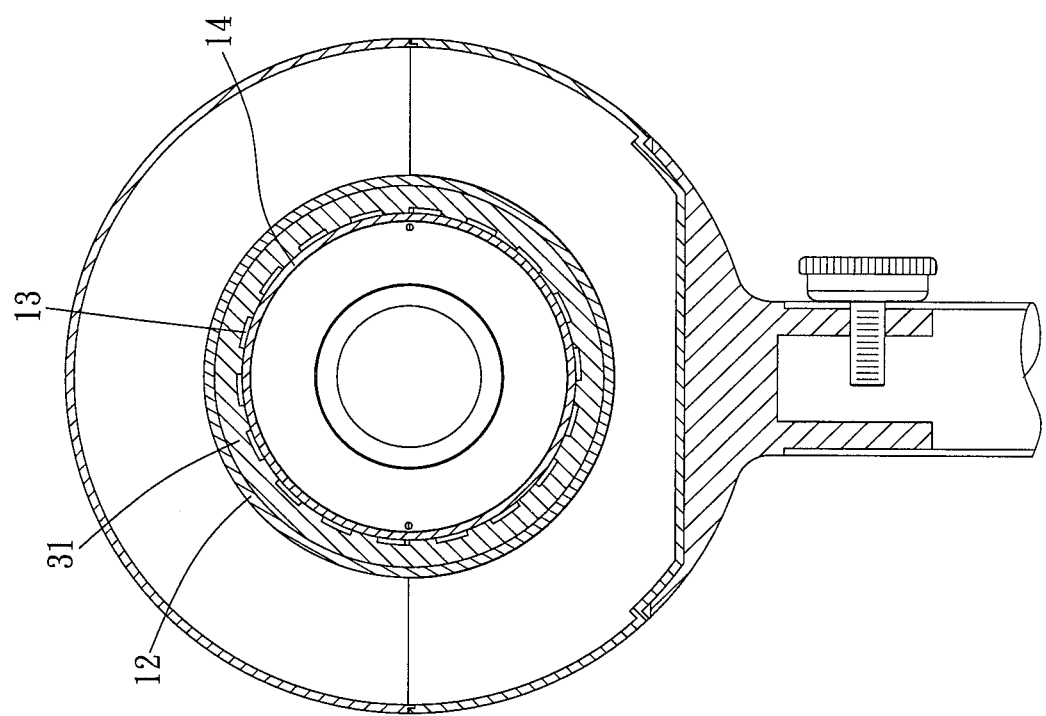
FIG. 6 is another cross-sectional view of the first preferred embodiment of the present invention.

Please refer to FIGS. 1 to 6 for a first preferred embodiment of the present invention. A light-magnetism providing apparatus 1 includes a shell body 10, a light generator 20 and a magnetic unit 30.

The shell body 10 defines a space 11 and includes a magnetism-shielding layer 12 outside the space 11. The light generator 20 is attached to the shell body 10 and emits light into the space 11. The magnetic unit 30 is attached to the shell body 10 and located by an inner side of the magnetism-shielding layer 12, part of magnetic line-lines of force of the magnetic unit 30 going outwardly is shielded by the magnetism-shielding layer 12, and part of magnetic line-lines of force of the magnetic unit 30 goes inwardly into the space 11, thus concentrating magnetic energy toward the space 11 without loss and harmonizing the light and magnetism.

In this embodiment, the magnetism-shielding layer 12 is a steel layer. However, the magnetism-shielding layer may be other materials which can or cannot shield magnetic lines of force.

The light generator 20 further includes a printed circuit board 21, at least one light source 22 disposed on the printed circuit board 21 and a light-guiding member 23 adjacent to the at least one light source 22, and the light-guiding member 23 guides the light into the space 11. The light generator 20 further includes a power part 24 electrically connected with the printed circuit board 21, wherein the power part 24 may be a battery or an electric port configured to be electrically connected to an external power such as Universal Serial Bus (USB) or the like. The light generator 20 can be turned on/off via a power switch 25 attached to the shell body 10. Preferably, the light generator 20 includes plurality of LED light source (or other types of light sources), the light-guiding member 23 includes a plurality of optical structures 231 which can provide a specific path to guide and/or even the light, thus improving interaction of the light and the magnetic field.

The magnetic unit 30 includes at least one unit magnetic region 31 disposed around the space 11, and each unit magnetic region 31 includes at least one pair of N-pole and S-pole which face the space 11. Each unit magnetic region 31 may be a single magnetic ring or composed of a plurality of magnetic members which are arranged annularly each including pairs of N-poles and S-poles. In this embodiment, the magnetic unit 30 includes a plurality of said unit magnetic regions 31, and the plurality of said unit magnetic regions 31 are separately disposed around the space 11.

Preferably, the shell body 10 further includes a first magnetism-penetrable layer 13, and the magnetic unit 30 is disposed between the first magnetism-penetrable layer 13 and the magnetism-shielding layer 12. Two opposite sides of the first magnetism-penetrable layer 13 include a plurality of embedding regions 131 which are separately arranged and a plurality of projection-recession structures 132 which are separately arranged, and each magnetic unit 30 is inlaid in one of the plurality of embedding regions 131 and corresponds to part of the plurality of projection-recession structures 132. The shell body 10 may further include a second magnetism-penetrable layer 14, and the first magnetism-penetrable layer 13 is disposed between the second magnetism-penetrable layer 14 and the magnetism-shielding layer 12. The first magnetism-penetrable layer 13 and the second magnetism-penetrable layer 14 may be connected with each other by an adhesive layer 15 attached therebetween. The second magnetism-penetrable layer 14 can serve as a protector, and has a smooth inner surface for comfortable use.

The shell body 10 further includes an inlet 16 communicating with the space 11 at an end thereof, and the shell body 10 further includes a magnetic disc 32 at other end thereof. The magnetic disc 32 faces the light generator 20, wherein magnet fields of the magnetic disc 32 and the magnetic unit 30 interacts with each other and the interaction thereof is effectively harmonized and improved.

Preferably, the shell body 10 includes two outer shells 17, which is easy to package and fabricate; the two outer shells 17 include a plurality of slots 171 at their respective ends, and the plurality of slots 171 make it easy to receive or/and hold the printed circuit board 21, the light-guiding member 23, the magnetic unit 30 and the magnetic disc 32; the light-magnetism providing apparatus 1 further includes a support 40, the shell body 10 may be detachably and adjustably connected to the support 40, and the bottom of the support 40 preferably includes a wheel assembly 41 for moving easily.

Figure 7:
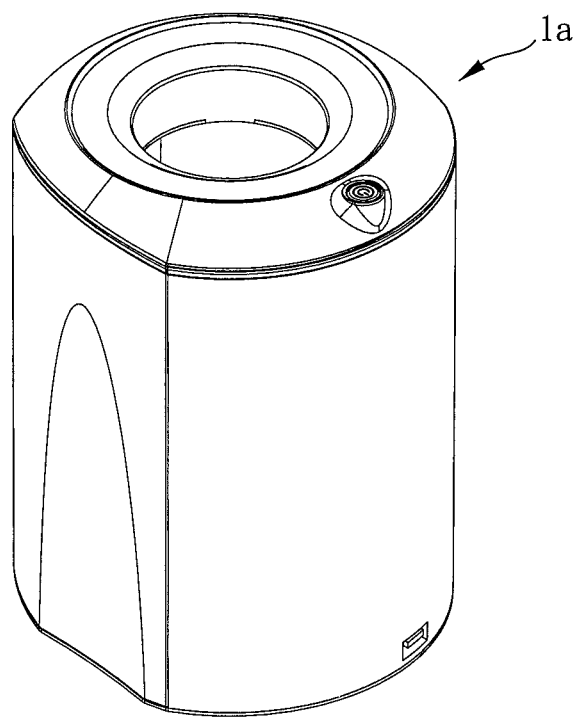
FIG. 7 is a perspective view of a second preferred embodiment of the present invention.
Figure 8:
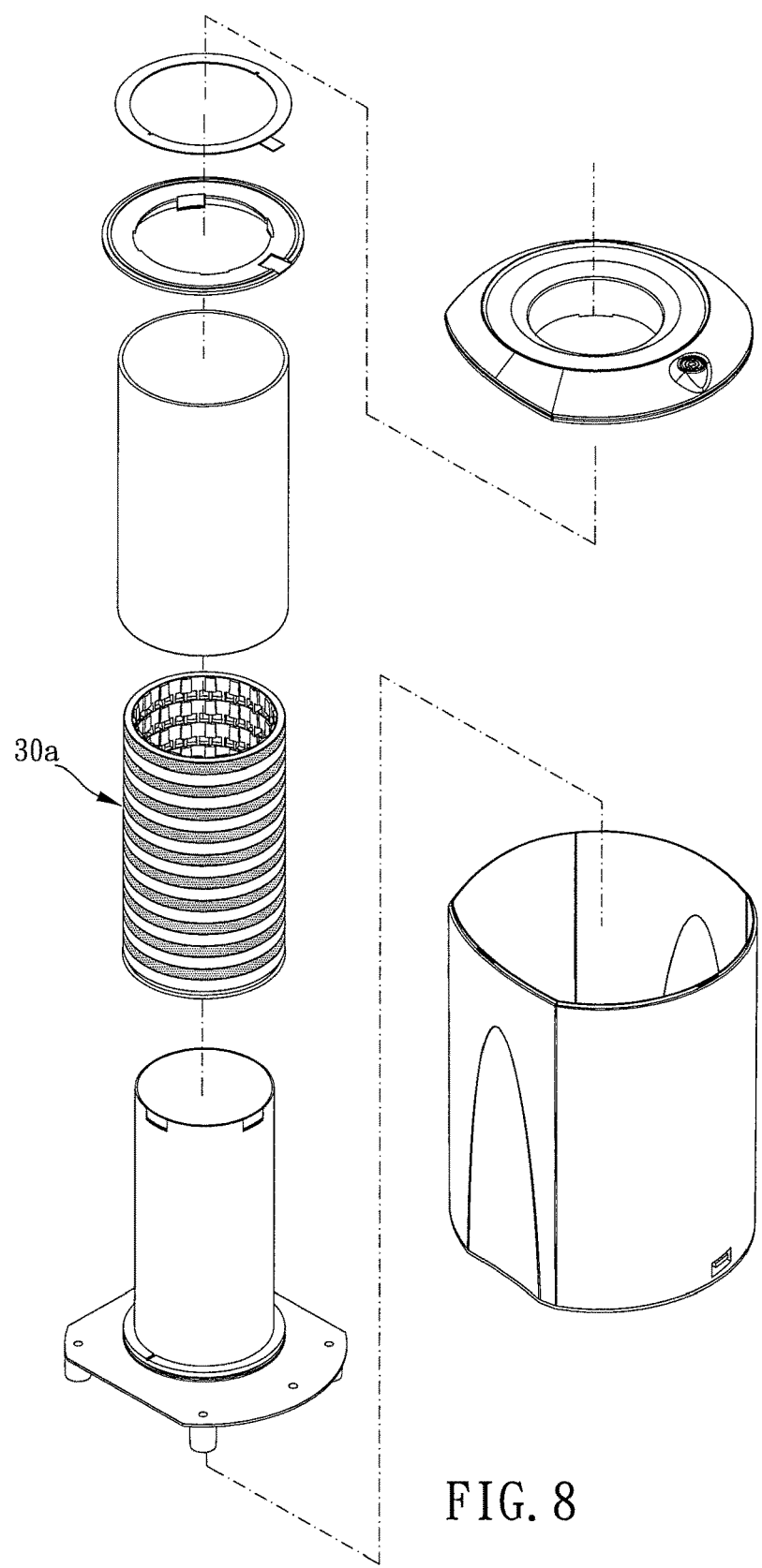
FIG. 8 is a breakdown view of the second preferred embodiment of the present invention.
Figure 9:
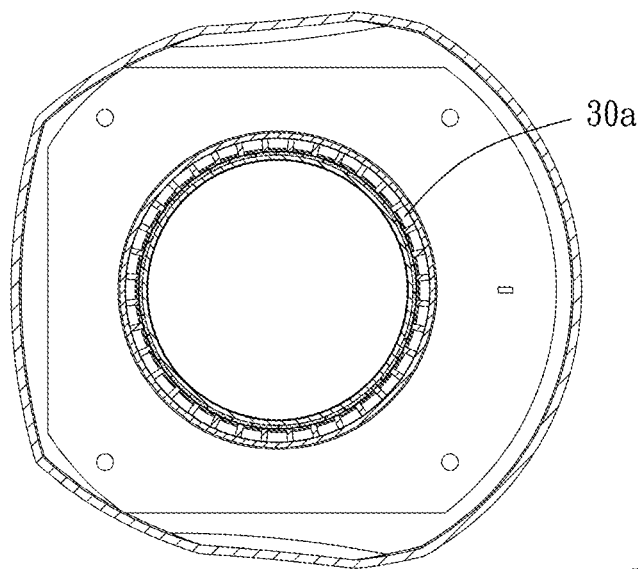
FIG. 9 is a cross-sectional view of the second preferred embodiment of the present invention.
Figure 10:
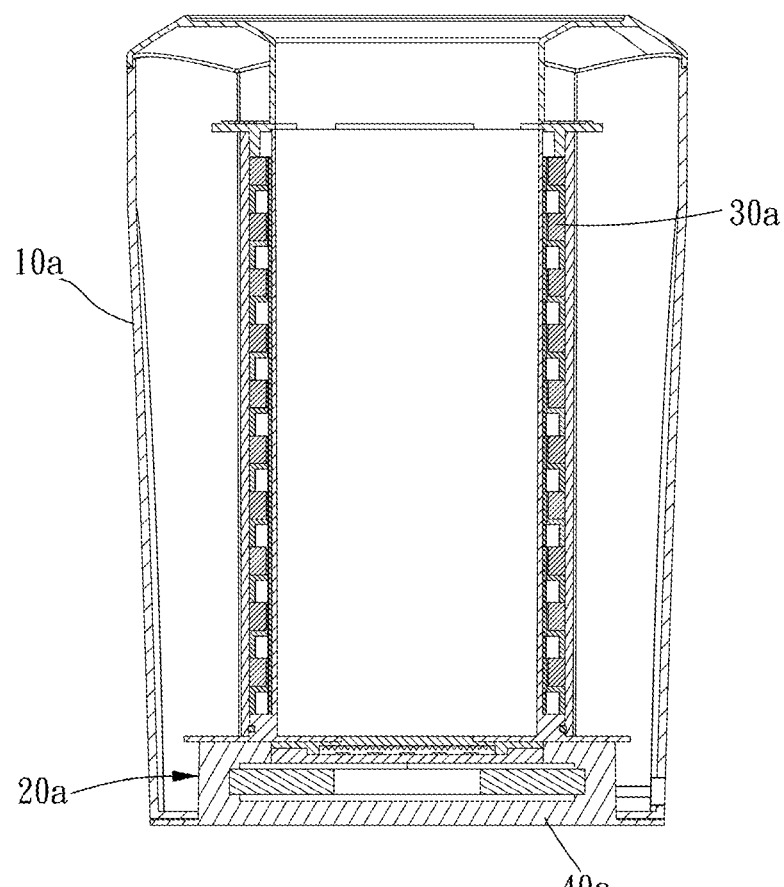
FIG. 10 is another cross-sectional view of a preferred embodiment of the present invention.

Please refer to FIGS. 7-10 for a second preferred embodiment of the present invention. In the second preferred embodiment, a shell body 10a of the light-magnetism providing apparatus 1a is integral with a base 40a for resting on a desk, and the light generator 20a and the magnetic unit 30a are located correspondingly above the base 40a.

Through the aforementioned structure, the light and magnetism are harmonized and resonates with the human body energy, so as to activate and balance the human body energy, mitigate influence of electromagnetic wave to the human body, and advance blood circulation and health. It can be used a plurality of times every day, and the period of time is not limited. It depends upon various persons.

The light-magnetism providing apparatus may be also applied to natural food or fluid such as tea, vegetables, fruits, cigarette, wine, soya sauce, vinegar, fermented bean curd and pickled materials etc, which can be indirectly advantageous to regulating and balancing the human body energy and be indirectly advantageous to health.

While we have shown and described various embodiments in accordance with the present invention, it should be clear to those skilled in the art that further embodiments may be made without departing from the scope of the present invention.

What is claimed is:

1. A light-magnetism providing apparatus, including: a shell body, defining a space and including a magnetism-shielding layer outside the space; a light generator, attached to the shell body, emitting light into the space; a magnetic unit, attached to the shell body and located by an inner side of the magnetism-shielding layer, part of magnetic lines of force of the magnetic unit going outwardly being shielded by the magnetism-shielding layer, part of the magnetic lines of force of the magnetic unit going inwardly into the space;

wherein the shell body further includes a first magnetism-penetrable layer, and the magnetic unit is disposed between the first magnetism-penetrable layer and the magnetism-shielding layer;

wherein two opposite sides of the first magnetism-penetrable layer include a plurality of embedding regions which are separately arranged and a plurality of projection-recession structures which are separately arranged, and each magnetic unit is inlaid in one of the plurality of embedding regions and corresponds to part of the plurality of projection-recession structures annularly.

2. The light-magnetism providing apparatus of claim 1, wherein the magnetism-shielding layer is a steel layer.

3. The light-magnetism providing apparatus of claim 1, wherein the magnetic unit includes at least one unit magnetic region disposed around the space, and each unit magnetic region includes at least one pair of N-pole and S-pole which face the space.

4. The light-magnetism providing apparatus of claim 3, wherein the magnetic unit includes a plurality of said unit magnetic regions, and the plurality of said unit magnetic regions are separately disposed around the space.

5. The light-magnetism providing apparatus of claim 1, wherein the shell body further includes an inlet communicating with the space at an end thereof, the shell body further includes a magnetic disc at other end thereof, and the magnetic disc faces the light generator.

6. The light-magnetism providing apparatus of claim 1, wherein the light generator further includes a printed circuit board, at least one light source disposed on the printed circuit board and a light-guiding member adjacent to the at least one light source, and the light-guiding member guides the light into the space.

7. The light-magnetism providing apparatus of claim 1, wherein the light generator includes a power part electrically connected with the printed circuit board, and the power part is a battery or an electric port configured to be electrically connected to an external power.

8. The light-magnetism providing apparatus of claim 1, wherein the light-guiding member includes a plurality of optical structures.

9. A light-magnetism providing apparatus including:
a shell body, defining a space and including a magnetism-shielding layer outside the space;
a light generator, attached to the shell body, emitting light into the space; a magnetic unit, attached to the shell body and located by an inner side of the magnetism-shielding layer, part of magnetic lines of force of the magnetic unit going outwardly being shielded by the magnetism-shielding layer, part of the magnetic lines of force of the magnetic unit going inwardly into the space;
wherein the shell body further includes a first magnetism-penetrable layer, and the magnetic unit is disposed between the first magnetism-penetrable layer and the magnetism-shielding layer;
wherein the shell body further includes a second magnetism-penetrable layer, and the first magnetism-penetrable layer is disposed between the second magnetism-penetrable layer and the magnetism-shielding layer;
wherein the first magnetism-penetrable layer and the second magnetism-penetrable layer are connected with each other by an adhesive layer attached therebetween.

* * * * *